(12) United States Patent
Nishizawa et al.

(10) Patent No.: US 7,615,749 B2
(45) Date of Patent: Nov. 10, 2009

(54) INFRARED LIGHT EMITTING DEVICE, INFRARED LIGHT DETECTING DEVICE, TIME-DOMAIN PULSED SPECTROMETER APPARATUS, AND INFRARED LIGHT EMITTING METHOD

(75) Inventors: Seizi Nishizawa, 2-15-4, Ozakudai, Hamura-shi, Tokyo 2050001 (JP); Toshiyuki Iwamoto, Hachioji (JP)

(73) Assignees: Japan Science and Technology Agency, Kawaguchi-Shi (JP); Seizi Nishizawa, Hamura-Shi (JP)

( * ) Notice: Subject to any disclaimer, the term of this patent is extended or adjusted under 35 U.S.C. 154(b) by 196 days.

(21) Appl. No.: 11/663,428

(22) PCT Filed: Sep. 27, 2005

(86) PCT No.: PCT/JP2005/017766

§ 371 (c)(1),
(2), (4) Date: Mar. 21, 2007

(87) PCT Pub. No.: WO2006/035780

PCT Pub. Date: Apr. 6, 2006

(65) Prior Publication Data

US 2007/0194253 A1      Aug. 23, 2007

(30) Foreign Application Priority Data

Sep. 30, 2004  (JP)  ............................. 2004-286579
Sep. 30, 2004  (JP)  ............................. 2004-286712

(51) Int. Cl.
*G01J 5/02* (2006.01)
(52) U.S. Cl. .............................. 250/339.07; 250/504 R
(58) Field of Classification Search ............ 250/339.07, 250/504 R
See application file for complete search history.

(56) References Cited

U.S. PATENT DOCUMENTS 5,914,497 A * 6/1999 Sherwin ....................... 257/21
6,320,191 B1 * 11/2001 Rudd ....................... 250/341.1

(Continued)

FOREIGN PATENT DOCUMENTS

JP        2002-277394        9/2002

(Continued)

*Primary Examiner*—David P Porta
*Assistant Examiner*—Jessica L Eley
(74) *Attorney, Agent, or Firm*—Edwards Angell Palmer & Dodge LLP

(57) ABSTRACT

There is provided an infrared light emitting device that is capable of polarizing emission light without causing loss of the emission light and having a simple configuration. Included are a photoconductive layer 22 which generates optical carriers upon being irradiated with pulsed excitation light; a pair of first antenna electrodes 21a for emitting infrared light, which are formed on the photoconductive layer 22 with a gap 32 disposed between tips thereof; a pair of second antenna electrodes 21b for emitting infrared light, which are formed on the photoconductive layer 22 and which are disposed with the gap 32 between tips thereof and having an angle with respect to the first antenna electrodes 21a; and a control unit for independently applying voltages to the first antenna electrodes 21a and the second antenna electrodes 21b. The voltage applied to the first antenna electrodes 21a and the voltage applied to the second antenna electrodes 21b may be selectively applied at different times or may be simultaneously applied with different phases.

20 Claims, 9 Drawing Sheets

U.S. PATENT DOCUMENTS 6,348,683 B1 * 2/2002 Verghese et al. .......... 250/214.1
6,627,914 B1 * 9/2003 Komiyama et al. ............ 257/29
2007/0171132 A1 * 7/2007 Utagawa et al. ....... 343/700 MS
2007/0296635 A1 * 12/2007 Popugaev et al. ...... 343/700 MS

FOREIGN PATENT DOCUMENTS

JP    2003-14620    1/2003

* cited by examiner

INFRARED LIGHT EMITTING DEVICE, INFRARED LIGHT DETECTING DEVICE, TIME-DOMAIN PULSED SPECTROMETER APPARATUS, AND INFRARED LIGHT EMITTING METHOD

TECHNICAL FIELD

The present invention relates to an infrared light emitting device, an infrared light detecting device, a time-domain pulsed spectrometer apparatus, and an infrared light emitting method.

BACKGROUND ART

With the realization of ultrashort pulsed laser technology in recent years, there has been remarkable progress in emission technology and detection technology of pulsed coherent electromagnetic waves in the infrared region (0.01 to 130 THz). As a result, time-domain pulsed spectroscopy using these pulsed electromagnetic waves in the infrared region has become possible, and there have been pioneering developments towards realization of time-domain pulsed spectrometer apparatuses.

Time-domain pulsed spectroscopy is a spectroscopic method in which the time-dependent electric-field intensity of a pulsed electromagnetic wave is measured, and by Fourier Transform that time-dependent data (time-domain data), the electric-field intensity and phase of each frequency component constituting that pulse are obtained. One feature of this spectroscopic method is that the measurement wavelength region is at the boundary between light and radio waves, which has been difficult to measure conventionally. Therefore, elucidation of the properties of novel materials and new phenomena using this spectroscopic method has been long anticipated. With conventional spectroscopy, only the electric-field intensity of an electromagnetic wave can be obtained; however, a unique feature possessed by this time-domain pulsed spectroscopy is its ability not only to measure the electric-field intensity (amplitude) of the electromagnetic waves but also to obtain the phase, by directly measuring the temporal variations of the electric-field intensity of the electromagnetic wave. Therefore, it is possible to obtain a phase-shift spectrum by comparing with a case where no sample is present. Because the phase-shift is proportional to the wave-number vector, it is possible to determine the dispersion relation of the sample using this spectroscopic method, and it is also possible to determine the dielectric constant of a ferroelectric crystal from this dispersion relation (see Patent Document 1).

FIG. 7 shows an example of a conventional time-domain pulsed spectrometer apparatus.

A femtosecond laser is used as a light source 1. For example, a mode-locked erbium (Er)-doped fiber laser is used as the light source 1. This mode-locked fiber laser 1 transmits, for example, a femtosecond laser pulse L1 with an average power of 10 mW, at a wavelength of 780 nm, a pulse width of 120 fs, and a repetition rate of 48.5 MHz.

The femtosecond laser pulse L1 emitted from the light source 1 is split by a beamsplitter 2. The femtosecond laser pulse at one side, serving as excitation pulsed laser light L2, is radiated onto pulsed-light emitting means (infrared light emitting device) 5. At this time, after the excitation pulsed laser light L2 is modulated by an optical chopper 3, it is focused by an objective lens 4. This pulsed-light emitting means 5 is, for example, a photoconductive antenna; when the excitation pulsed laser light L2 is radiated, an instantaneous current flows, and a far-infrared pulse L3 is emitted. This far-infrared pulse (THz (terahertz) light pulse) L3 is guided by parabolic mirrors 6 and 7 and irradiates a measurement sample 8. Reflected or transmitted pulsed light (in the figure, it is transmitted pulsed light) L3' from the sample 8 is guided to detecting means 12 via parabolic mirrors 9 and 10.

The other laser light split at the beamsplitter 2 is guided to the detecting means 12 to serve as detection pulsed laser light L4. Because this detecting means 12, which is also a photoconductive antenna, is irradiated with the detection pulsed laser light L4 and becomes conductive only momentarily, it is possible to detect the electric-field intensity of the reflected or transmitted pulsed light from the sample 8 arriving at that instant as an electrical current. A time-domain signal of the electric-field intensity of the reflected or transmitted pulsed light from the sample 8 can be obtained by imposing a time delay at predetermined time intervals to the detection pulsed laser light L4 with respect to the excitation pulsed laser light L2 using optical delay means 13 (or 14). In this figure, in addition to the optical delay means 13 (or 14) for time-domain signal measurement, an optical delay means 14 (or 13) for time-origin adjustment may also be provided.

The time-division data of the electric-field intensity of the reflected or transmitted pulsed light from the sample 8 is processed by signal processing means. In other words, the amplitude and phase shift spectra of the electric-field intensity of the reflected or transmitted pulsed electromagnetic wave from the sample 8 is obtained by sending the data to a computer 17 via a lock-in amplifier 16, and then recording it as time-domain data and subjecting a time-domain data set to Fourier transform processing in the computer 17 to convert it to the oscillation frequency (frequency) domain.

FIG. 8 shows the pulsed light emitting means 5. The pulsed light emitting means uses a photoconductive switch element (antenna electrode) with a dipole antenna structure formed on a photoconductive layer made of low-temperature growth gallium arsenide (LT(low temperature)-GaAs). Thus, to generate terahertz emission light L3, the terahertz emission light L3 is obtained by irradiating such a pulsed light emitting means 5 with excitation pulsed laser light L2 to excite free carriers, namely electrons and holes, and performing ultra-high-speed current modulation. In other words, when the pulsed light emitting means 5, to which a bias current is applied, is irradiated with the excitation pulsed laser light L2, the electric field is oscillated. When the electric field is oscillated, due to the oscillating current, the terahertz emission light L3 having a broad spectral distribution over a frequency range defined by a temporal width Δt of the excitation pulsed laser light L2 irradiating the pulsed-electromagnetic-wave emitting element 5 is obtained.

The detecting means 12 has the same configuration as the pulsed light emitting means 5 shown in FIG. 8. When this detecting means 12 is simultaneously irradiated with the terahertz light L3' transmitted through the sample and the detection pulsed laser light L4, it is possible to measure the intensity of the terahertz light L3' transmitted through the sample during the time period when the detection pulsed laser light L4 is irradiated.

FIG. 9 shows antenna electrodes 21 formed on a photoconductive layer 22 made of LT-GaAs. Gold (Au) is used as the antenna electrodes 21. As shown in the magnified view of an antenna peripheral portion 21c at the right of this figure, a gap of about 5 μm is formed between the pair of antenna electrodes 21, and the width of the antenna electrodes is about 10 μm.

To perform polarization analysis using such a time-domain pulsed spectrometer apparatus, a known technique for obtaining a desired polarization involves inserting a polarizer into the light path (see Patent Document 2).

FIG. 10 shows a sectional view, along A-A', of the antenna peripheral portion 21c shown in FIG. 9. As is clear from this figure, the photoconductive layer 22 is formed on a substrate 23 which is made of semi-insulated gallium arsenide (SI (semi-insulated)-GaAs).

When used as the pulsed light emitting means 5, the excitation pulsed laser light L2 is irradiated towards the antenna electrode 21 side (one side surface) (from the top in the figure) as viewed from the photoconductive layer 22. The terahertz emission light L3 is emitted towards the substrate 23 side (other side surface) (towards the bottom in the figure) as viewed from the photoconductive layer 22.

When used as the detecting means 12, the detection pulsed laser light L4 is irradiated towards the antenna electrode 21 side (one side) (from the top in the figure) as viewed from the photoconductive layer 22. The terahertz light L3' transmitted through the sample is irradiated from the substrate 23 side (other side) (from the bottom in the figure) as viewed from the photoconductive layer 22.

Patent Document 1:
Japanese Unexamined Patent Application, Publication No. 2002-277394.
Patent Document 2:
Japanese Unexamined Patent Application, Publication No. 2003-014620.

DISCLOSURE OF INVENTION

However, because the technology disclosed in Patent Document 1 is nothing more than using a pair of antenna electrodes (FIG. 9), the polarization of the emitted terahertz light is always in a single fixed direction only.

If a desired polarization is obtained by inserting a polarizer into the light path, as in the technology disclosed in Patent Document 2, it is possible to obtain a target polarization component; however, the other light components are not used at all and are completely lost.

On the other hand, a method involving rotating the pulsed light emitting means itself in order to rotate the polarization of the emitted terahertz light may be considered; however, it is essential, then, to carry out control so that the excitation laser pulsed light follows the rotating pulsed light emitting means. Also, arranging cables for applying a voltage to the rotating pulsed light emitting means becomes a problem.

When using the pulsed light emitting means 5 and the detection means 12 having the configuration described above, the following problems occur.

As shown in FIG. 11, the SI-GaAs used in the substrate 23 has an absorption band due to phonons at 100 to 400 $cm^{-1}$. In other words, it exhibits a characteristic whereby, above 100 $cm^{-1}$, the transmittance drops suddenly, and at 240 $cm^{-1}$ or more, even above 300 $cm^{-1}$, almost no light is transmitted.

Because SI-GaAs absorbs the excitation laser pulsed light, it is necessary to employ a structure in which the excitation pulsed laser light L2 is radiated from the antenna electrode 21 side at the side opposite the substrate 23 (one side). Therefore, when used as the pulsed light emitting means 5, it is necessary to employ a structure in which the terahertz light emitted by the antenna electrodes 21 is transmitted through the substrate 23. Thus, because SI-GaAs has an absorption band at 100 to 400 $cm^{-1}$, as described above, there is a problem in that it is not possible to sufficiently extract terahertz light in a wide band.

Also when used as the detecting means 12, the pulsed laser light L3' transmitted through the sample is transmitted from the substrate 23 side and detected; therefore, absorption due to phonons in the SI-GaAs becomes a problem.

The present invention has been conceived in light of the circumstances described above, and an object thereof is to provide an infrared light emitting device, a time-domain pulsed spectrometer apparatus, and an infrared light emitting method in which polarization of emitted light is possible with a simple configuration without causing loss of the emitted light.

Furthermore, an object of the present invention is to provide an infrared light emitting device, an infrared light detecting device, and a time-domain pulsed spectrometer apparatus enabling measurement over a wide band without being affected by absorption in the substrate.

In order to solve the problems described above, the infrared light emitting device, the time-domain pulsed spectrometer apparatus, and the infrared light emitting method of the present invention employ the following solutions.

Specifically, an infrared light-emitting device according to the present invention comprises a photoconductive layer which is irradiated with pulsed excitation light to generate optical carriers; a pair of first antenna electrodes for emitting infrared light, which are formed on the photoconductive layer with a gap disposed between tips thereof; a pair or a plurality of pairs of second antenna electrodes for emitting infrared light, which are formed on the photoconductive layer with the gap between tips thereof and having an angle with respect to the first antenna electrodes; and a control unit for independently applying voltages to the first antenna electrodes and the second antenna electrodes.

Because the second antenna electrodes having a different angle from the first antenna electrodes are provided and these electrodes are independently controlled by the control unit, it is possible to emit from the second antenna electrodes infrared light having a different polarization from the infrared light emitted from the first antenna electrodes.

The control unit of the infrared light-emitting device described above selectively switches between a voltage applied to the first antenna electrodes and a voltage applied to the second antenna electrodes.

Because the voltages applied to the antenna electrodes are selectively switched, it is possible to select, at desired time intervals, the light polarization corresponding to the position of each antenna electrode.

The control unit of the infrared light-emitting device described above applies voltages with different phases to the first antenna electrodes and the second antenna electrodes.

Because voltages with different phases are applied to each antenna electrode, circularly polarized light is possible. In other words, by simultaneously applying, for example, sine-wave voltages with different phases to each antenna electrode, it is possible to obtain circularly polarized emission light.

A time-domain pulsed spectrometer apparatus according to the present invention comprises a light source for generating pulsed excitation light; and one of the infrared light-emitting devices described above.

Because the infrared light emitting device described above is provided, it is possible to provide a time-domain pulsed spectrometer apparatus which can measure a polarization-dependent measurement object.

An infrared light emitting method of the present invention comprises applying a voltage to a pair of first antenna electrodes for emitting infrared light, which are formed on a photoconductive layer that generates optical carriers upon being irradiated with pulsed excitation light and which are disposed with a gap between tips thereof; and applying a voltage to a pair or a plurality of pairs of second antenna electrodes for emitting infrared light, which are formed on the photoconductive layer and which are disposed with the gap between tips thereof and so as to have an angle with respect to the first antenna electrodes.

Because a voltage is applied to the second antenna electrodes, which have a different angle from the first antenna electrodes, it is possible to emit from the second antenna electrodes infrared light having a different polarization from the infrared light emitted from the first antenna electrodes.

The voltage applied to the first antenna electrodes and the voltage applied to the second antenna electrodes may be selectively applied at different times or they may be simultaneously applied with different phases.

According to the invention described above, it is possible to realize the following advantage. Specifically, because the antenna electrodes disposed so as to have different angles are provided, it is possible to realize polarization of the emission light without loss and with a simple configuration.

In order to solve the problems described above, the infrared light emitting device, the infrared light detecting device, and the time-domain pulsed spectrometer apparatus of the present invention employ the following means.

Specifically, an infrared light emitting device according to the present invention comprises a photoconductive layer for generating optical carriers upon being irradiated with pulsed excitation light; a pair of antenna electrodes for emitting infrared light, which are formed on one side surface of the photoconductive layer and which are disposed with a gap between tips thereof; and an infrared-light-transmitting optics for transmitting infrared light, which is formed at the other side surface of the photoconductive layer in a region corresponding at least to the gap.

Because an infrared-light-transmitting optics that transmits infrared light is used, it is possible to losslessly emit infrared light from the other side surface of the photoconductive layer.

The infrared-light-transmitting optics may be formed in a region corresponding to the gap formed between at least one pair of the antenna electrodes; in addition to the case where it is disposed only in the region corresponding to this gap, it may also be disposed on the entirety, including the region corresponding to this gap. For example, the substrate provided at the other side surface of the photoconductive layer may be formed of diamond-like carbon, which transmits far-infrared light.

The infrared-light-transmitting optics may be disposed in direct contact on the other side surface of the photoconductive layer, or it may be disposed indirectly, with a substrate portion that is thinner than the thickness of the surrounding substrate disposed therebetween. In such a case, because the substrate portion is thin, it is possible to significantly reduce the absorption of infrared light.

Here, the term "transmitting infrared light" means, for example, a transmittance of 50% or more at the wavelength of the infrared light. More specifically, the infrared-light-transmitting optics may be diamond-like carbon, silicon, silicon-based ceramic, or a polymer material such as white polyethylene.

An infrared light emitting device according to the present invention comprises a photoconductive layer for generating optical carries upon being irradiated with pulsed excitation light; a pair of antenna electrodes for emitting infrared light, which are formed on one side surface of the photoconductive layer and which are disposed with a gap between tips thereof; and a pulsed-excitation-light transmitting optics for transmitting pulsed excitation light, which is formed at the other side surface of the photoconductive layer in a region corresponding at least to the gap.

Because a pulsed-excitation-light transmitting optics that transmits pulsed excitation light is used, it is possible to losslessly irradiate pulsed excitation light from the other side surface of the photoconductive layer. Also, because the infrared light emitted by the antenna electrode is emitted towards one side surface of the photoconductive layer, when a substrate that exhibits absorption due to phonons is disposed at the other side surface, it can be losslessly emitted without passing through this substrate.

The pulsed-excitation-light transmitting optics may be formed in a region corresponding to the gap formed between at least one pair of the antenna electrodes; in addition to the case where it is disposed only in the region corresponding to this gap, it may also be disposed on the entirety, including the region corresponding to the gap. For example, the substrate disposed at the other side surface of the photoconductive layer may be formed of diamond-like carbon, which transmits the pulsed excitation light.

The pulsed-excitation-light transmitting optics may be disposed in direct contact on the other side surface of the photoconductive layer, or it may be indirectly disposed, with a substrate portion that is thinner than the thickness of the surrounding substrate disposed therebetween. Accordingly, because the substrate portion is thin, it is possible to significantly reduce the absorption of the pulsed excitation light.

Here, the term "transmits pulsed excitation light" means, for example, a transmittance of 50% or more at the wavelength of the pulsed excitation light. More specifically, other than diamond-like carbon, glasses such as quartz may be used for the pulsed-excitation-light transmitting optics.

An infrared light emitting device of the present invention comprises a photoconductive layer for generating optical carriers upon being irradiated with pulsed excitation light; and a pair of antenna electrodes for emitting infrared light, which are formed on one side surface of the photoconductive layer and which are disposed with a gap between tips thereof; wherein a void is formed at the other side surface of the photoconductive layer in a region corresponding to the gap.

Because a void is formed at the other side surface of the photoconductive layer, when the pulsed excitation light is radiated so as to pass through this void, it is possible to guide the pulsed excitation light in the photoconductive layer without loss.

More concretely, the substrate may be provided at the other side surface of the photoconductive layer, and a substrate in which the void is formed only at the region corresponding to the gap between the pair of antenna electrodes may be used.

An infrared light detecting device of the present invention comprises a photoconductive layer for generating optical carriers upon being irradiated with pulsed excitation light; a pair of antenna electrodes for detecting infrared light, which are formed on one side surface of the photoconductive layer and which are disposed with a gap between tips thereof; and an infrared-light-transmitting optics for transmitting infrared light, which is formed at the other side surface of the photoconductive layer in a region corresponding at least to the gap.

Because the infrared-light-transmitting optics that transmits infrared light is used, it is possible to guide the infrared light from the other side surface and to detect the infrared light without loss.

The infrared-light-transmitting optics may be formed in a region corresponding to the gap formed between the pair of antenna electrodes; in addition to the case where it is formed only in the region corresponding to this gap, it may also be formed on the entirety, including the region corresponding to the gap.

More specifically, as the infrared-light-transmitting optics, it is possible to use diamond-like carbon, silicon, silicon-based ceramic, or a polymer material such as white polyethylene.

An infrared light detecting device of the present invention comprises a photoconductive layer for generating optical carriers upon being irradiated with pulsed excitation light; a pair of antenna electrodes for detecting infrared light, which are formed on one side surface of the photoconductive layer and which are disposed with a gap between tips thereof; and a pulsed-excitation-light transmitting optics for transmitting the pulsed excitation light, which is formed at the other side surface of the photoconductive layer in a region corresponding at least to the gap.

Because the pulsed-excitation-light transmitting optics that transmits the pulsed excitation light is used, by guiding the pulsed excitation light from the other side surface and making the infrared light incident from the one side surface, it is possible to detect the infrared light without loss due to phonon absorption in the substrate material and so forth.

The pulsed-excitation-light transmitting optics may be formed in the region corresponding to the gap formed between the pair of antenna electrodes; in addition to the case where it is disposed only in the region corresponding to this gap, it may be disposed on the entirety, including the region corresponding to the gap.

More specifically, as the pulsed-excitation-light transmitting optics, it is possible to use diamond-like carbon or a glass such as fused silica.

An infrared light detecting device of the present invention comprises a photoconductive layer for generating optical carriers upon being irradiated with pulsed excitation light; and a pair of antenna electrodes for detecting infrared light, which are formed on one side surface of the photoconductive layer and which are disposed with a gap between tips thereof; wherein a void is formed at the other side surface of the photoconductive layer in a region corresponding to the gap.

Because the void is formed at the other side surface of the photoconductive layer, if the infrared light is guided so as to pass through this void, it is possible to detect the infrared light without loss.

More specifically, the substrate may be disposed at the other side surface of the photoconductive layer, and a substrate in which the void is formed only at the region corresponding to the gap between the pair of antenna electrodes may be used.

A time-domain pulsed spectrometer apparatus of the present invention comprises a light source for a pulsed excitation radiation; and the infrared light emitting device and/or the infrared light detecting device described above.

Because an infrared light emitting device that reduces the absorption of excitation light and/or an infrared light detecting device that reduces the absorption of emitted light is provided, it is possible to provide a time-domain pulsed spectrometer apparatus in which measurement is possible in a wide band.

According to the present invention, because an excitation-light transmitting optics or an infrared-light transmitting optics is disposed or, alternatively, a void is formed, in a portion corresponding to a gap between a pair of antenna electrodes, it is possible to provide an infrared light emitting device, an infrared light detecting device, and a time-domain pulsed spectrometer apparatus in which it is possible to measure in a wide band without being affected by absorption in the substrate.

BRIEF DESCRIPTION OF DRAWINGS

FIG. 1 is a plan view showing a pattern of antenna electrodes according to a first embodiment of the present invention.

FIG. 2 is a plan view showing a modification of the pattern of antenna electrodes according to a first embodiment of the present invention.

FIG. 3 is a cross-sectional view showing a second embodiment of the present invention.

FIG. 4 is a graph showing the transmittance of diamond-like carbon.

FIG. 5 is a diagram showing a method of fabricating a terahertz light emitting device of the second embodiment.

FIG. 6 is a sectional view showing a third embodiment of the present invention.

FIG. 7 is a diagram showing, in outline, a time-domain pulsed spectrometer.

FIG. 8 is a perspective view showing pulsed light emitting means.

FIG. 9 is a plan view showing the pattern of conventional antenna electrodes.

FIG. 10 is a sectional view showing an antenna portion.

FIG. 11 is a graph showing the transmittance of GaAs.

BEST MODE FOR CARRYING OUT THE INVENTION

Embodiments of the present invention will be described below with reference to the drawings.

Figure 1:
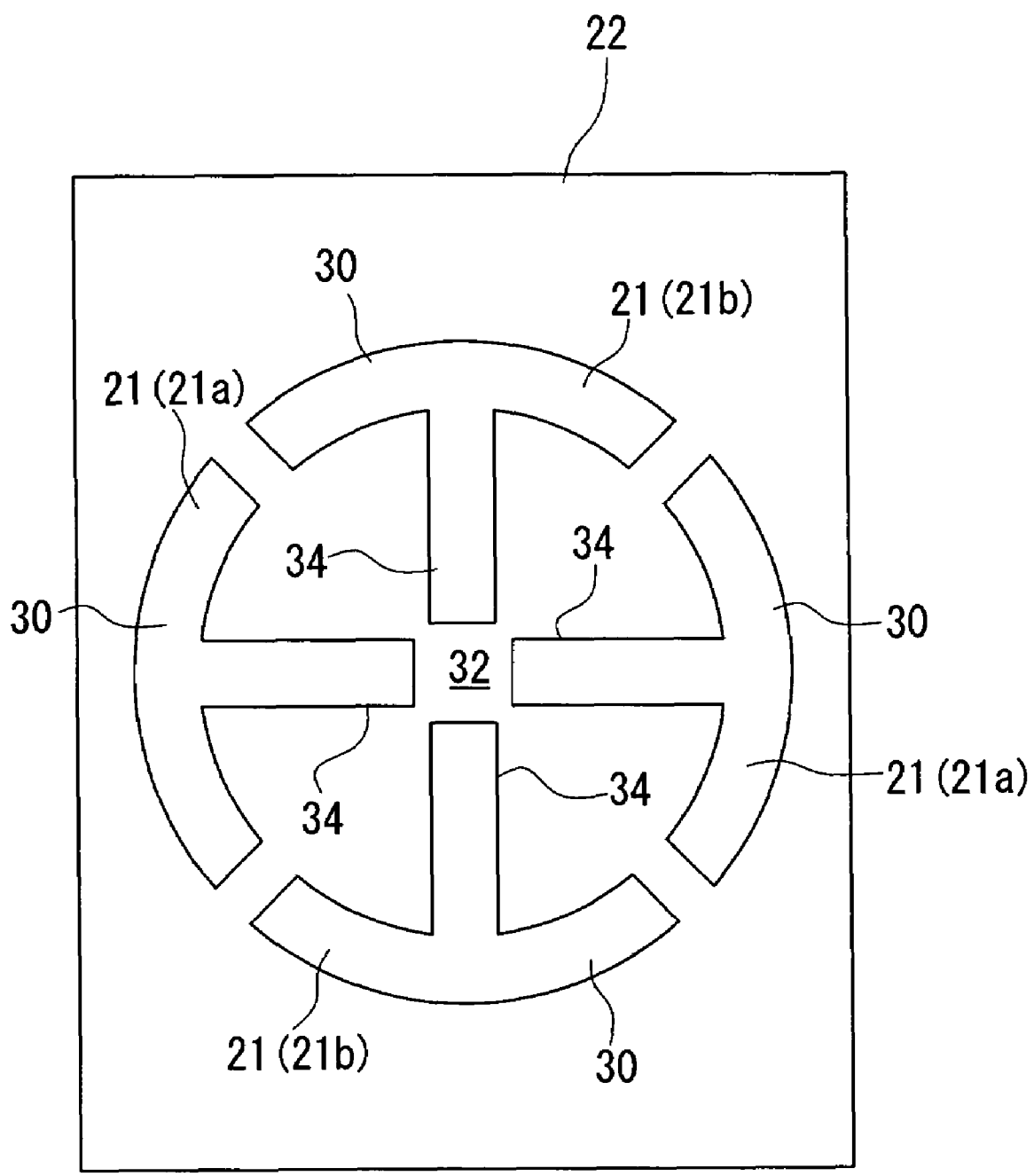
[FIG. 1]
Figure 7:
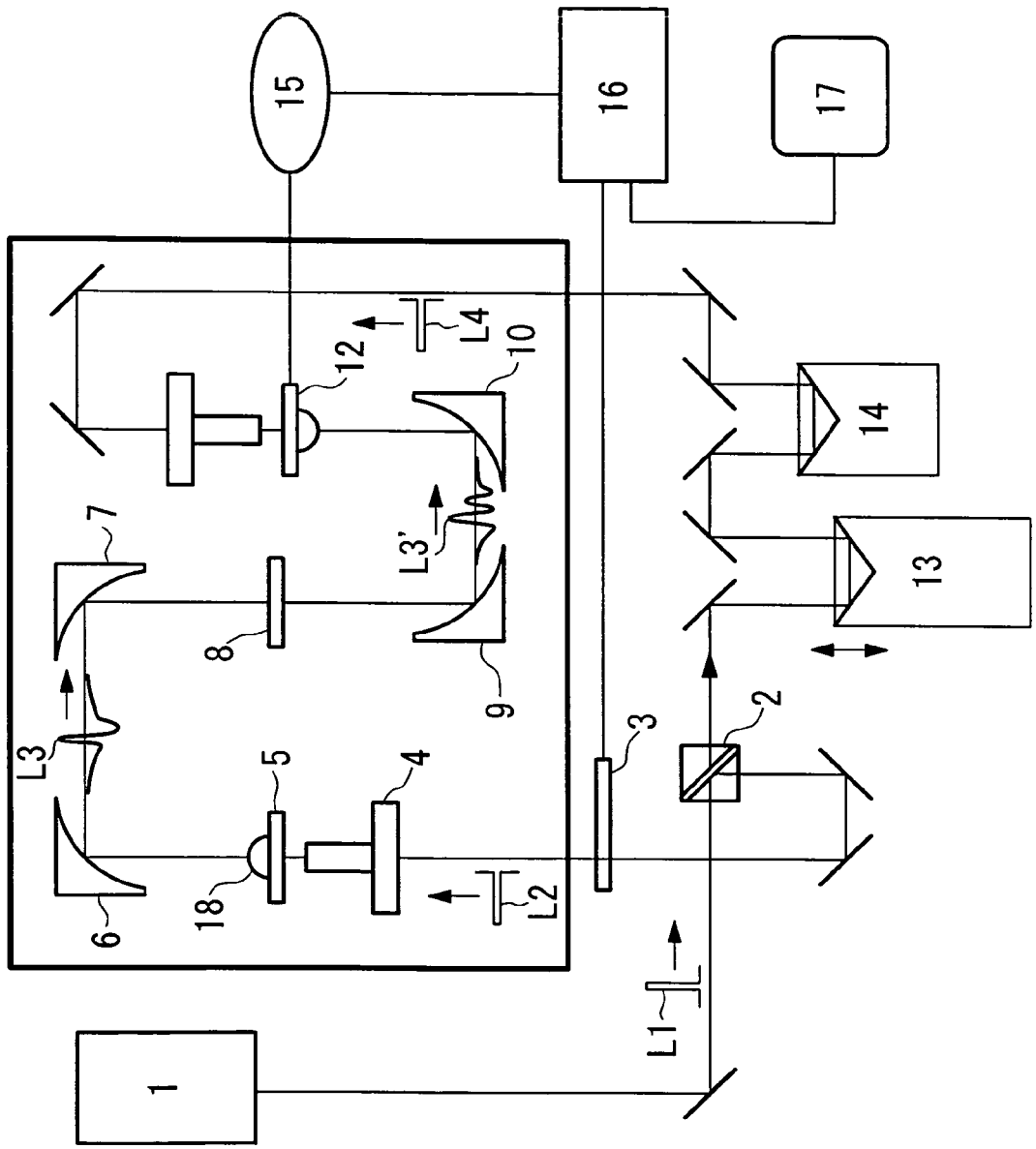
[FIG. 7]
Figure 8:
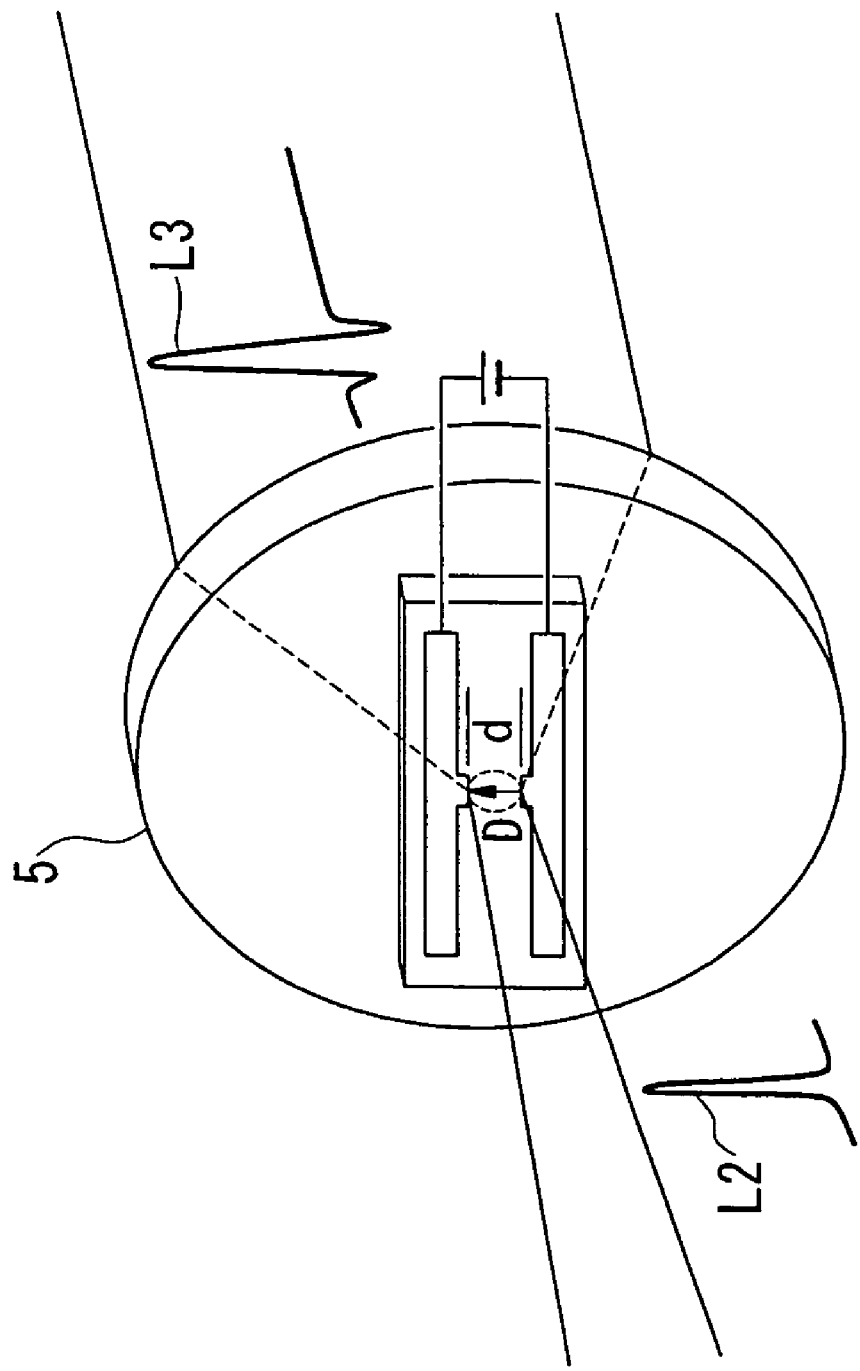
[FIG. 8]

FIG. 1 shows the principal parts of a terahertz light emitting device (infrared light emitting device) according to a first embodiment of the present invention. The terahertz light emitting device of this embodiment is employed in the time-domain pulsed spectrometer described using FIG. 7.

As shown in FIG. 1, antenna electrodes 21 are formed by vapor deposition on a photoconductive layer 22 deposited on a substrate. The antenna electrodes 21 are formed of gold (Au). The photoconductive layer 22 is formed of low-temperature growth gallium arsenide (LT-GaAs).

A pair of first antenna electrodes 21a are disposed at the left and right positions in the figure, and a pair of second antenna electrodes 21b are disposed at the top and bottom positions in the figure. In other words, the orientations of the first antenna electrodes 21a and the second antenna electrodes 21b are disposed so as to differ by substantially 90° in plan view (so as to be substantially orthogonal).

A feed portion 30 that is connected to a lead line (not shown in the drawing) is disposed at a base portion of each antenna electrode 21. At a tip portion of each antenna electrode 21, an antenna portion 34, which is positioned so as to form a gap 32 between the tip portions of the opposing antenna electrodes 21, is disposed. The pattern of these antenna electrodes 21 is suitably determined according to the frequency band of the terahertz light to be emitted.

The gap 32 is shared by the first antenna electrodes 21a and the second antenna electrodes 21b. In other words, there are common gaps between the first antenna electrodes 21a and between the second antenna electrodes 21b.

Although not shown in the drawing, a control unit for independently applying voltages to the first antenna electrodes and the second antenna electrodes is provided. The control unit has a function for controlling the timing and voltage waveform for the applied voltage.

The terahertz light-emitting device with the above-described configuration is used as follows.

First, a voltage is applied only to the first antenna electrodes 21a by the control unit, at predetermined time intervals. In this case, no voltage is applied to the second antenna electrodes 21b. Under these conditions, the antenna electrodes 21 are irradiated with excitation pulsed laser light L2 (see FIG. 7). Because a voltage is applied only to the first antenna electrodes 21a, it is possible to obtain only a fixed polarization according to the position of the first antenna electrodes 21a.

Next, a voltage is applied only to the second antenna electrodes 21b by the control unit, at predetermined time intervals. In this case, no voltage is applied to the first antenna electrodes 21a. Under these conditions, the antenna electrodes 21 are irradiated with the excitation pulsed laser light L2 (see FIG. 7). It is thus possible to obtain only a fixed polarization according to the position of the second antenna electrodes 21b.

In this way, by selectively switching between the voltages applied to each of the antenna electrodes 21a, b using the control unit, it is possible to obtain, at different times, different polarizations according to the position of the antenna electrodes 21a, b.

The terahertz light-emitting device of this embodiment can also be used as follows.

Voltages are applied by the control unit to the first antenna electrodes 21a and the second antenna electrodes 21b simultaneously and at different phases. More specifically, a sine-wave voltage is applied to the first antenna electrodes 21a, and a sine wave having the same amplitude and period but a different phase is applied to the second antenna electrodes 21b. Under these conditions, the antenna electrodes 21 are irradiated with the excitation pulsed laser light L2 (see FIG. 7). By doing so, circularly-polarized terahertz light is emitted.

If not only the phase but also the amplitude of the sine-wave voltage applied to the second antenna electrodes 21b is made to differ, elliptically polarized terahertz light is emitted.

By using the device in this way, it is possible to perform measurement, for example, with a circular-dichroism detector or the like.

As described above, with the terahertz light emitting device of this embodiment, the pairs of antenna electrodes 21 are disposed so as to have different angles from each other. Therefore, instead of rotating the terahertz light emitting device itself, it is possible to emit terahertz light having a desired polarization plane without providing an optical polarizer in the light path.

Therefore, it is possible to realize polarization of emitted light using a simple configuration and without causing loss of the emitted light.

Figure 2:
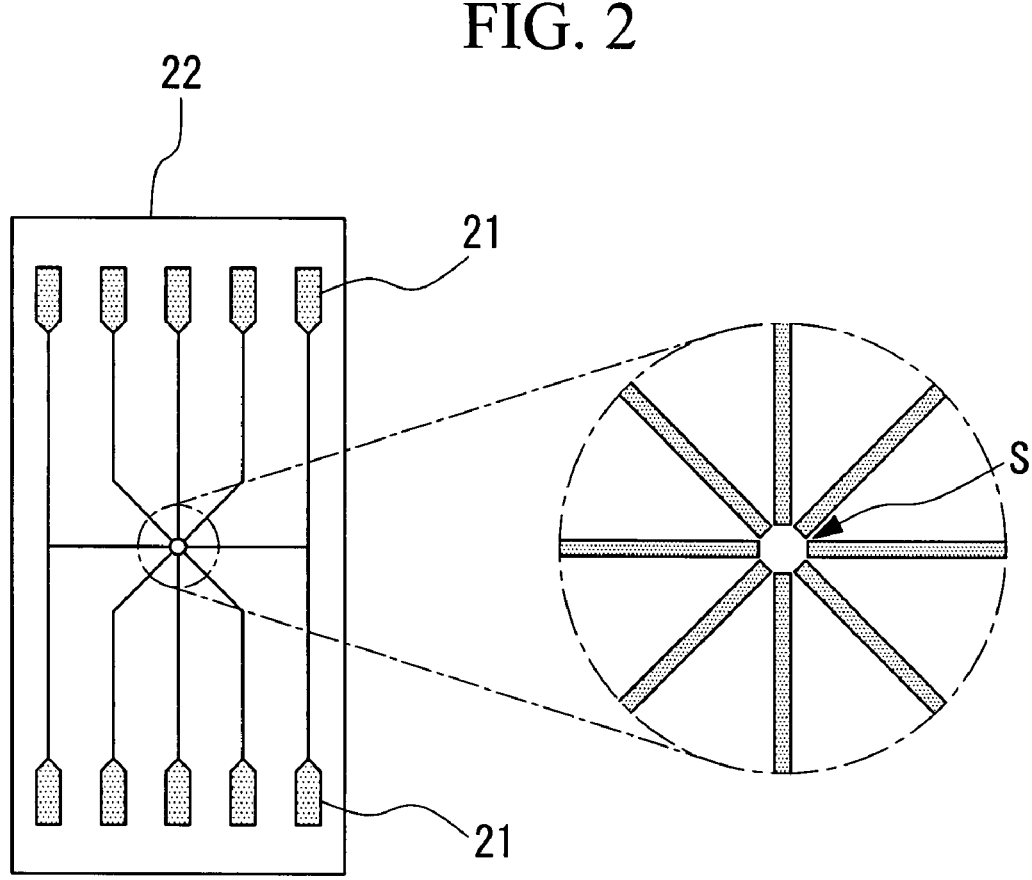
[FIG. 2]

A configuration using two pairs of antenna electrodes has been described in this embodiment; however, the present invention is not limited to this. For example, as shown in FIG. 2, a configuration in which three pairs of antenna electrodes are disposed at different angles is also possible. By doing so, it is possible to control the light polarization more finely. A minute gap s is provided between the adjacent tips of each antenna electrode.

Although a terahertz light emitting device which is applied to time-domain pulsed spectrometers has been described in this embodiment, the present invention in not limited to this; it is also possible to use it in other applications.

Next, a second embodiment of the present invention will be described using FIGS. 3 to 5.

Figure 3:
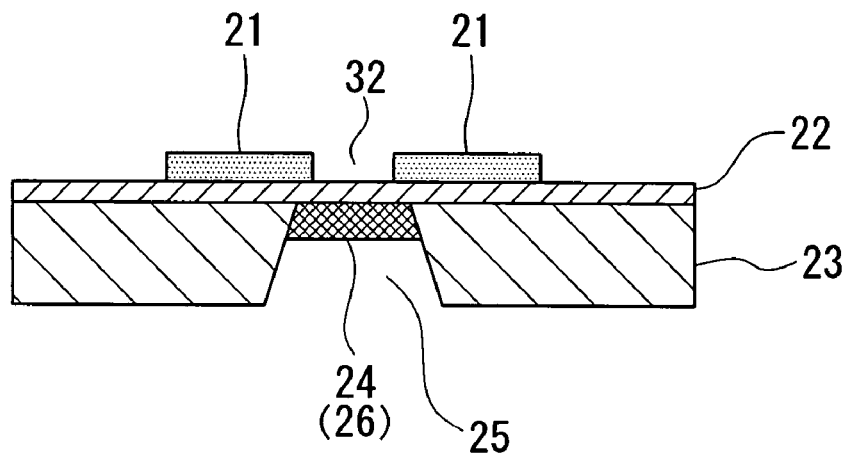
[FIG. 3]

FIG. 3 shows the principal parts of a terahertz light emitting device (infrared light emitting device) and a terahertz light detecting device (infrared light detecting device) according to an embodiment of the present invention. The terahertz light emitting device and the terahertz light detecting device use the same configuration but differ in terms of their operating mode, namely, emitting terahertz light L3 or having terahertz light L3' transmitted through a sample incident thereon.

Figure 10:
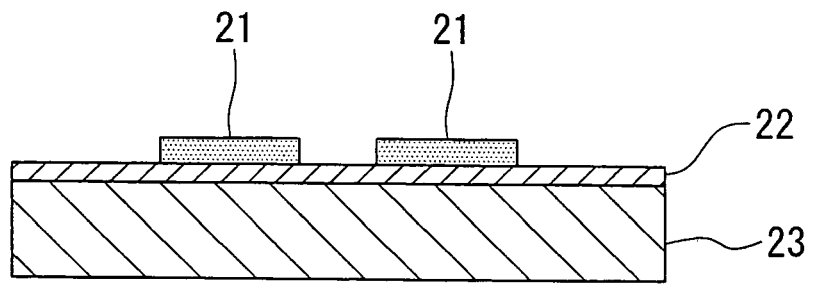
[FIG. 10]
Figure 11:
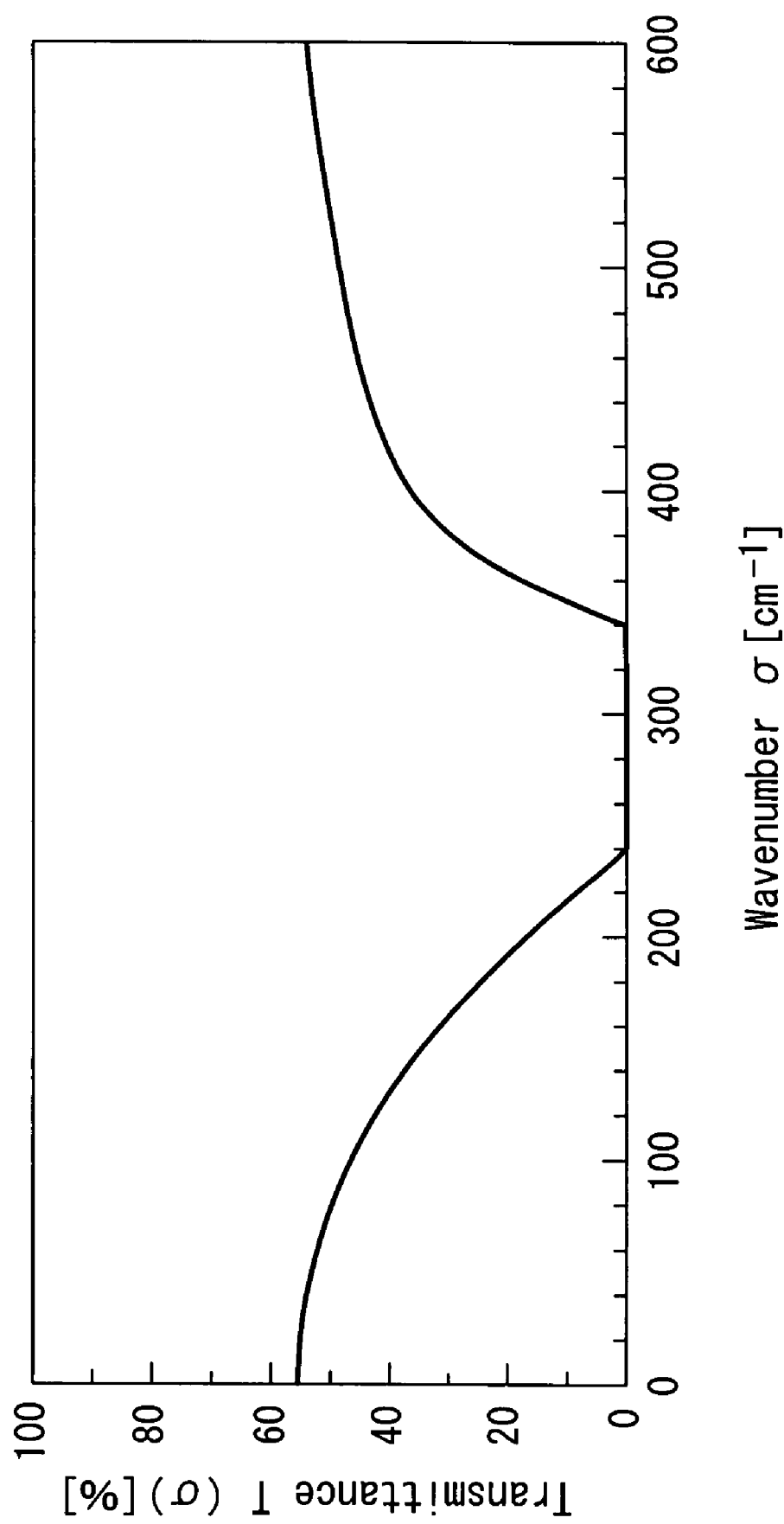
[FIG. 11]

FIG. 3 shows a sectional view of an antenna peripheral portion of the terahertz light emitting device and the terahertz light detecting device, corresponding to FIG. 10 described above. The terahertz light emitting device and the terahertz light detecting device of this embodiment are applied to the time-domain pulsed spectrometer described using FIG. 7.

The terahertz light emitting device and the terahertz light detecting device include a SI-GaAs substrate 23, a photoconductive layer 22 made of LT-GaAs formed on this substrate 23 by low-temperature growth, and a pair of antenna electrodes 21 formed of gold (Au), which are vapor deposited on the photoconductive layer 22.

Tips of the pair of antenna electrodes 21 oppose each other, and a gap 32 is formed between these tips.

Viewed from the photoconductive layer 22, at the substrate 23 side (the other side surface), a void 25 is formed in the region corresponding to the gap 32. An infrared-light-transmitting optics 24 formed of diamond-like carbon (hereinafter referred to as "DLC") is disposed in this void 25. Instead of DLC, it is also possible to use a material that transmits infrared light, such as silicon, silicon-based ceramic, or a polymer material like white polyethylene. The transmittance of the infrared-light-transmitting optics 24 is preferably 50% or more at infrared wavelengths.

The infrared-light-transmitting optics 24 is disposed so as to be in direct contact with the photoconductive layer 22. Instead of direct contact between the infrared-light-transmitting optics 24 and the photoconductive layer 22, it is also possible to dispose the infrared-light-transmitting optics 24 indirectly such that a substrate portion that is thinner than the thickness of the surrounding substrate 23 is disposed between the infrared-light-transmitting optics 24 and the photoconductive layer 22. With this configuration, it is also possible to drastically reduce the absorption of the substrate 23.

Figure 4:
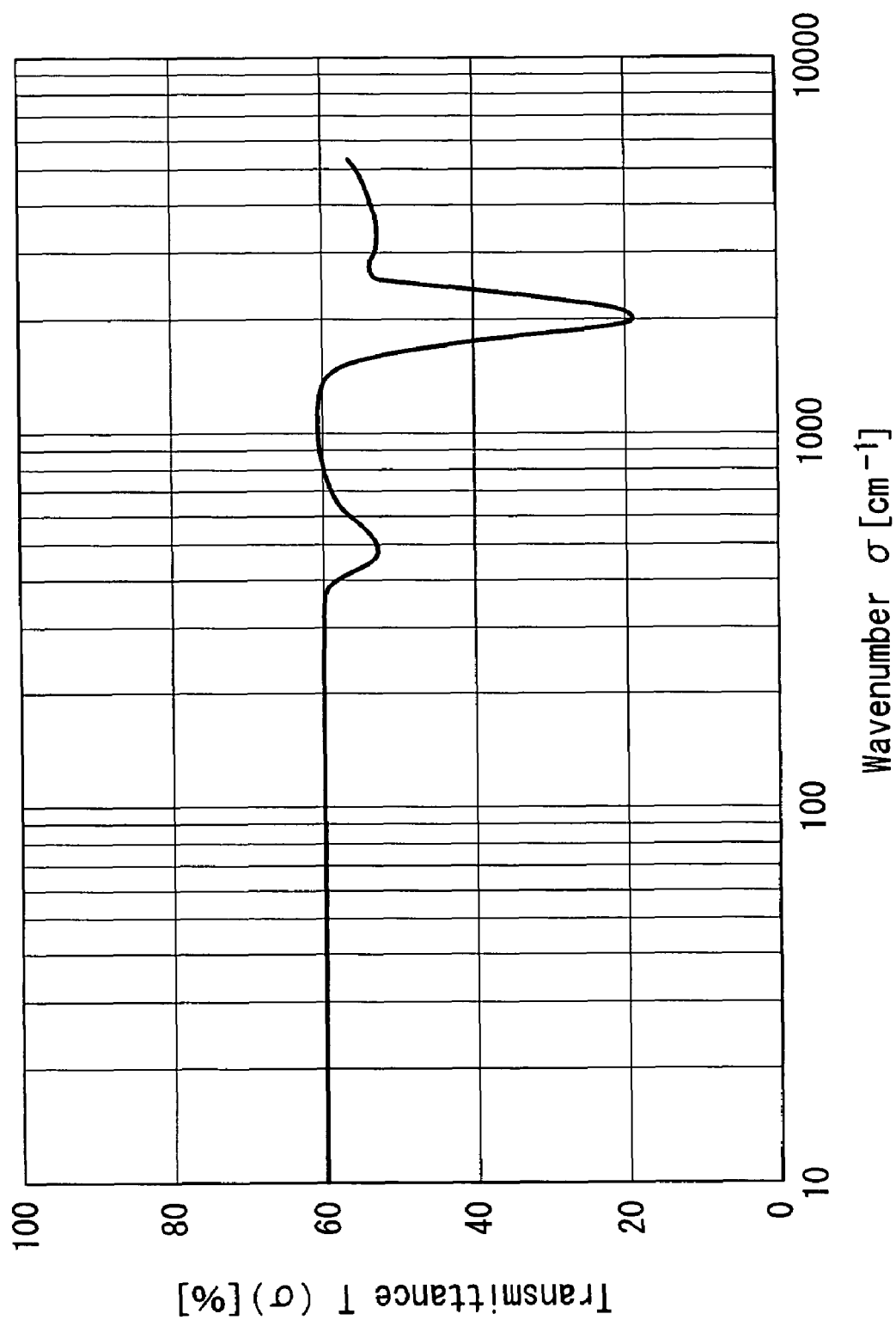
[FIG. 4]
Figure 5:
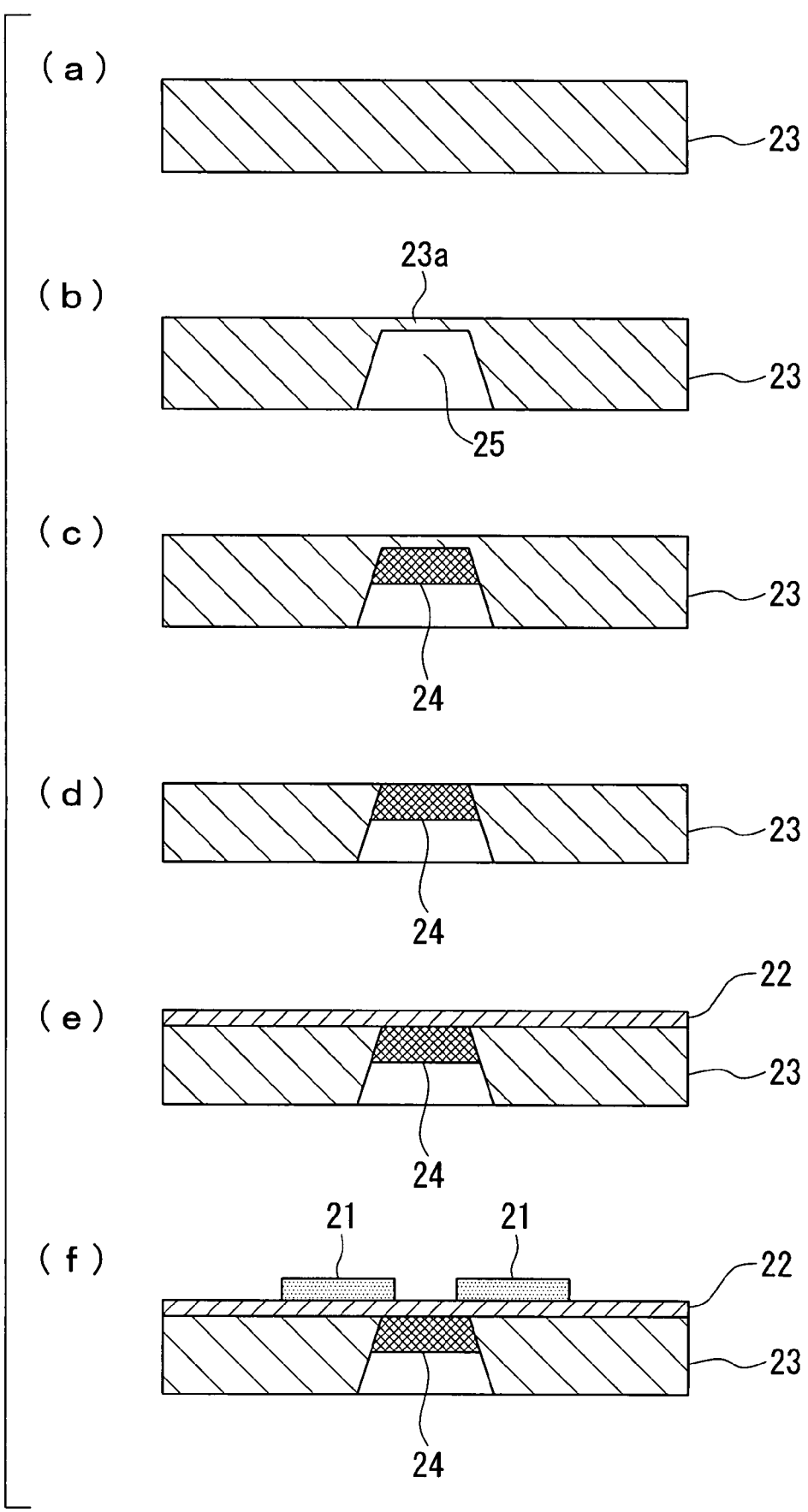
[FIG. 5]
Figure 9:
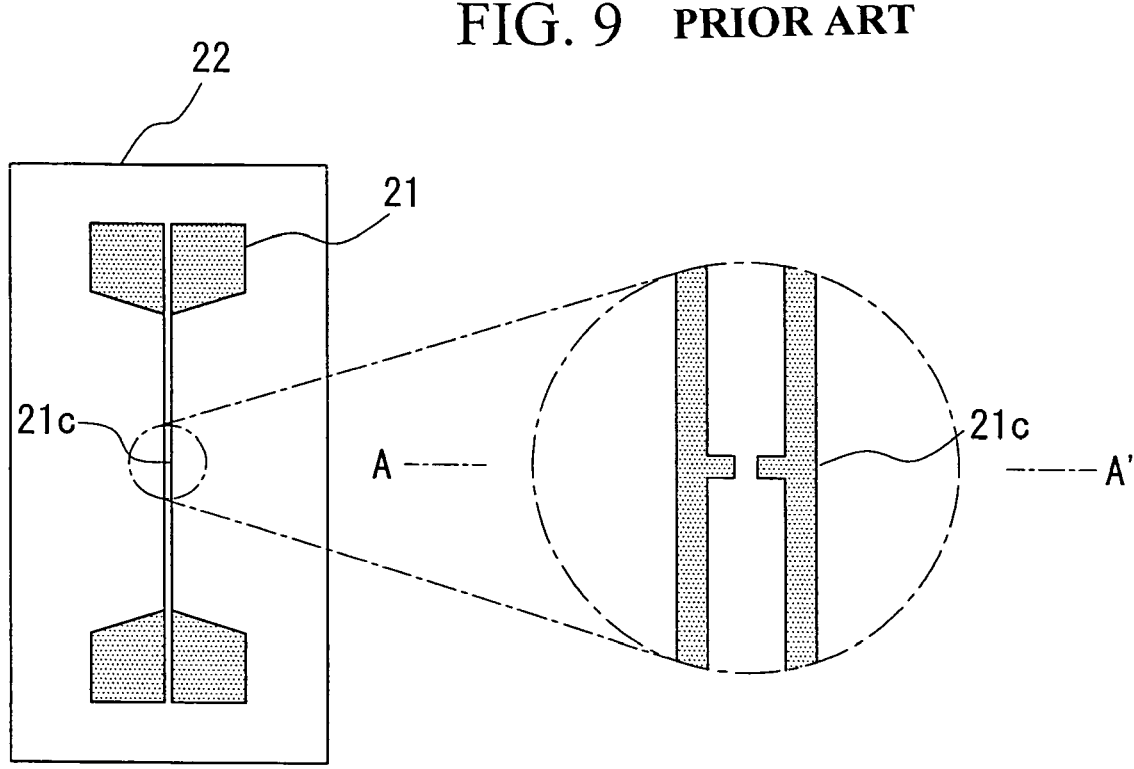
[FIG. 9]

FIG. 4 shows the transmittance of the DLC (vertical axis) versus wavenumber (horizontal axis). As is clear from this graph, the DLC is different from the SI-GaAs (see FIG. 9) used in the substrate 23 in that there is no absorption band at 100 to 400 $cm^{-1}$. Therefore, the terahertz light emitted by the antenna electrodes 21 and the terahertz light detected by the antenna electrodes 21 can be emitted and collected without being affected by phonons in the substrate 23, which enables measurement over a wide band.

When used as a terahertz light emitting device, by suitably adjusting the thickness of the infrared-light-transmitting optics 24, it is possible to relatively intensify specific frequency components by multiple reflection of the infrared light. For example, if the optical path difference between a front-surface reflection and a rear-surface reflection is set to 60 μm in the infrared wavelength region, it is possible to generate an electromagnetic wave component at about 5 THz.

Next, a method of fabricating the terahertz light emitting device and the terahertz light detecting device with the above-described configuration will be described using FIG. 5.

First, an unprocessed substrate 23 is prepared (a). Next, leaving a thin-walled portion 23a, etching is performed to form the void 25 (b).

Then, by filling from the thin-walled section 23a side, DLC is deposited inside the void 25 to form the infrared-light-transmitting optics 24 (c). In this step, the thickness of the infrared-light-transmitting optics 24 is set to a desired value.

Then, after removing the top surface of the substrate 23 so as to remove the thin-walled portion 23a of the substrate 23 (d), the photoconductive layer 22 is formed by growing LT-GaAs (e). Here, it is utilized that the DLC has the property of easily growing LT-GaAs.

Finally, the antenna electrodes 21 are vapor deposited on the photoconductive layer 22 (f).

Next, a case in which an excitation-light-transmitting optics 26 is used instead of the infrared-light-transmitting optics 24 will be described. In this case, the basic configuration is the same as that of the terahertz light emitting device and the terahertz light detecting device shown in FIG. 1, but the directions in which excitation light and terahertz light are incident or emitted differ. DLC or quartz glass is preferable as the excitation-light-transmitting optics.

In FIG. 3, the emitted terahertz light L3 or the terahertz light L3' transmitted through a sample (see FIG. 7) is irradiated from the antenna electrode 21 side, and excitation pulsed laser light L2 or detection pulsed laser light L4 (see FIG. 7) is transmitted through the excitation-light-transmitting optics 26 disposed at the substrate 22 side and irradiates the antenna electrodes 21.

According to this embodiment, the following operational advantages are realized.

Because the infrared-light-transmitting optics 24 is disposed in the area corresponding to the gap 32 between the antenna electrodes 21, when used as a terahertz light emitting device, it is possible to make the excitation pulsed laser light L2 (see FIG. 5) incident from the antenna electrode 21 side and to emit the terahertz emitted light L3 (see FIG. 5) so that it passes through the infrared-light-transmitting optics 24. Accordingly, it is possible to realize lossless incidence and emission, which enables measurement in a wide band.

When using it as a terahertz light detecting device, it is possible to make the terahertz light L3' transmitted through the sample (see FIG. 7) incident so as to pass through the infrared-light-transmitting optics 24 and to make the detection pulsed laser light L4 (see FIG. 7) incident from the antenna electrode 21 side. Accordingly, it is possible to realize lossless incidence and emission, which enables measurement in a wide band.

On the other hand, because the excitation-light-transmitting optics 26 is disposed in the area corresponding to the gap 32 between the antenna electrodes 21, when used as a terahertz light emitting device, it is possible to make the excitation pulsed laser light L2 (see FIG. 7) incident so as to pass through the excitation-light-transmitting optics 26 and to emit the terahertz emitted light L3 (see FIG. 7) from the antenna electrode 21 side so as not to pass through the substrate. Accordingly, it is possible to realize lossless incidence and emission, which enables measurement in a wide band.

When used as a terahertz light detecting device, it is possible to make the detection pulsed laser light L4 (see FIG. 7) incident so as to pass through the excitation-light-transmitting optics 26 and to make the terahertz light L3' transmitted through the sample (see FIG. 7) incident from the antenna electrode 21 side. Accordingly, it is possible to realize lossless incidence and emission, which enables measurement in a wide band.

In the present embodiment, the infrared-light-transmitting optics 24 or the excitation-light-transmitting optics 26 is disposed only in the region corresponding to the gap 32 between the antenna electrodes 21. However, the present invention is not limited to this; it is also possible to use DLC for the entire substrate 23 and to make the excitation light incident from the substrate 23 side.

In the present embodiment, the thickness of the infrared-light-transmitting optics 24 or the excitation-light-transmitting optics 26 is smaller than the surrounding substrate 23. However, this thickness is not limited in the present embodiment; it is also possible to use a thickness substantially the same as that of the surrounding substrate 23. Accordingly, it is possible to directly contact an optics disposed at the substrate 23 side with the transmitting optics 24 and 26, which enables lossless coupling to be realized.

Figure 6:
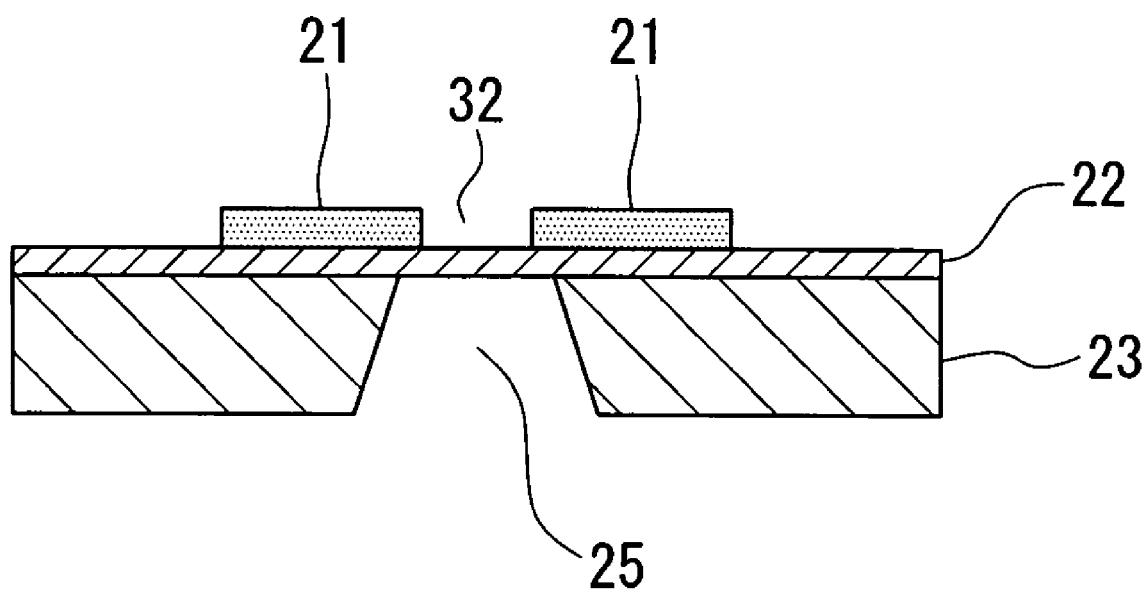
[FIG. 6]

Next, a third embodiment of the present invention will be described using FIG. 6.

This embodiment differs from the second embodiment in that a void is simply formed, and an excitation-light-transmitting optics is not used. The other parts are the same as those in the second embodiment.

A void 25 is formed so as to pass through the substrate 23 in a region corresponding to the gap 32 between the antenna electrodes 21. By providing such a void 25, when used as a terahertz light emitting device, excitation pulsed laser light L2 (see FIG. 7) is made incident so as to pass through the void 25, and terahertz emitted light L3 (see FIG. 7) is emitted from the antenna electrode 21 side so as to pass through the substrate 23. Accordingly, it is possible to realize lossless incidence and emission, which enables measurement in a wide band.

When used as a terahertz light detecting device, the terahertz light L3' transmitted through the sample (see FIG. 7) is made incident so as to pass through the void 25, and detection pulsed laser light L4 (see FIG. 7) is incident from the antenna electrode 21 side. Accordingly, it is possible to realize lossless incidence and emission, which enables measurement in a wide band.

In each embodiment above, a terahertz light emitting device and a terahertz light detecting device applied to a time-domain pulsed spectrometer have been described. However, the infrared-light emitting device and infrared-light detecting device of the present invention are not limited to this, and it is possible to use them in other applications.

The invention claimed is:

1. An infrared light-emitting device comprising:
a photoconductive layer which is irradiated with pulsed excitation light to generate optical carriers;
a pair of first antenna electrodes for emitting infrared light, which are formed on the photoconductive layer with a gap disposed between tips thereof;
a pair or a plurality of pairs of second antenna electrodes for emitting infrared light, which are formed on the photoconductive layer with the gap between tips thereof and having an angle with respect to the first antenna electrodes; and
a control unit for independently applying voltages to the first antenna electrodes and the second antenna electrodes.

2. An infrared light-emitting device according to claim 1, wherein the control unit selectively switches between a voltage applied to the first antenna electrodes and a voltage applied to the second antenna electrodes.

3. An infrared light-emitting device according to claim 1, wherein the control unit applies voltages with different phases to the first antenna electrodes and the second antenna electrodes.

4. A time-domain pulsed spectrometer apparatus comprising:
a light source for generating pulsed excitation light; and
an infrared light-emitting device according to claim 1.

5. An infrared light emitting method comprising:
applying a voltage to a pair of first antenna electrodes for emitting infrared light, which are formed on a photoconductive layer that generates optical carriers upon being irradiated with pulsed excitation light and which are disposed with a gap between tips thereof; and
applying a voltage to a pair or a plurality of pairs of second antenna electrodes for emitting infrared light, which are formed on the photoconductive layer and which are disposed with the gap between tips thereof and so as to have an angle with respect to the first antenna electrodes.

6. An infrared light emitting device comprising:
a photoconductive layer for generating optical carriers upon being irradiated with pulsed excitation light;
a pair of antenna electrodes for emitting infrared light, which are formed on one side surface of the photoconductive layer and which are disposed with a gap between tips thereof; and
an infrared-light-transmitting optics for transmitting infrared light, which is formed at the other side surface of the photoconductive layer in a region corresponding at least to the gap.

7. A time-domain pulsed spectrometer apparatus comprising:
a light source for oscillating pulsed excitation light; and
an infrared light emitting device according to claim 6.

8. The time-domain pulsed spectrometer apparatus of claim 7, further comprising:
an infrared light detecting device comprising
a photoconductive layer for generating optical carriers upon being irradiated with pulsed excitation light;
a pair of antenna electrodes for detecting infrared light, which are formed on one side surface of the photoconductive layer and which are disposed with a gap between tips thereof; and
a pulsed-excitation-light transmitting optics for transmitting the pulsed excitation light, which is formed at the other side surface of the photoconductive layer in a region corresponding at least to the gap.

9. The time-domain pulsed spectrometer apparatus of claim 7, further comprising:
an infrared light detecting device comprising
a photoconductive layer for generating optical carriers upon being irradiated with pulsed excitation light; and
a pair of antenna electrodes for detecting infrared light, which are formed on one side surface of the photoconductive layer and which are disposed with a gap between tips thereof;
wherein a void is formed at the other side surface of the photoconductive layer in a region corresponding to the gap.

10. An infrared light emitting device comprising:
a photoconductive layer for generating optical carriers upon being irradiated with pulsed excitation light;
a pair of antenna electrodes for emitting infrared light, which are formed on one side surface of the photoconductive layer and which are disposed with a gap between tips thereof; and
a pulsed-excitation-light transmitting optics for transmitting pulsed excitation light, which is formed at the other side surface of the photoconductive layer in a region corresponding at least to the gap.

11. A time-domain pulsed spectrometer apparatus comprising:
a light source for oscillating pulsed excitation light; and
an infrared light emitting device according to claim 10.

12. An infrared light emitting device comprising:
a photoconductive layer for generating optical carriers upon being irradiated with pulsed excitation light; and
a pair of antenna electrodes for emitting infrared light, which are formed on one side surface of the photoconductive layer and which are disposed with a gap between tips thereof;
wherein a void is formed at the other side surface of the photoconductive layer in a region corresponding to the gap.

13. A time-domain pulsed spectrometer apparatus comprising:
a light source for oscillating pulsed excitation light; and
an infrared light emitting device according to claim 12.

14. An infrared light detecting device comprising:
a photoconductive layer for generating optical carriers upon being irradiated with pulsed excitation light;
a pair of antenna electrodes for detecting infrared light, which are formed on one side surface of the photoconductive layer and which are disposed with a gap between tips thereof; and
an infrared-light-transmitting optics for transmitting infrared light, which is formed at the other side surface of the photoconductive layer in a region corresponding at least to the gap.

15. A time-domain pulsed spectrometer apparatus comprising:
a light source for oscillating pulsed excitation light; and
an infrared light detecting device according to claim 14.

16. An infrared light detecting device comprising:
a photoconductive layer for generating optical carriers upon being irradiated with pulsed excitation light;
a pair of antenna electrodes for detecting infrared light, which are formed on one side surface of the photoconductive layer and which are disposed with a gap between tips thereof; and
a pulsed-excitation-light transmitting optics for transmitting the pulsed excitation light, which is formed at the other side surface of the photoconductive layer in a region corresponding at least to the gap.

17. A time-domain pulsed spectrometer apparatus comprising:
a light source for oscillating pulsed excitation light; and
an infrared light detecting device according to claim 16.

18. An infrared light detecting device comprising:
a photoconductive layer for generating optical carriers upon being irradiated with pulsed excitation light; and
a pair of antenna electrodes for detecting infrared light, which are fainted on one side surface of the photoconductive layer and which are disposed with a gap between tips thereof;
wherein a void is formed at the other side surface of the photoconductive layer in a region corresponding to the gap.

19. A time-domain pulsed spectrometer apparatus comprising:
  a light source for oscillating pulsed excitation light; and
  an infrared light detecting device according to claim 18.

20. The time-domain pulsed spectrometer apparatus of claim 7, further comprising:
  an infrared light detecting device comprising
    a photoconductive layer for generating optical carriers upon being irradiated with pulsed excitation light;
    a pair of antenna electrodes for detecting infrared light, which are formed on one side surface of the photoconductive layer and which are disposed with a gap between tips thereof; and
    an infrared-light-transmitting optics for transmitting infrared light, which is formed at the other side surface of the photoconductive layer in a region corresponding at least to the gap.

* * * * *